United States Patent [19]
Sasagawa

[11] Patent Number: 5,375,607
[45] Date of Patent: Dec. 27, 1994

[54] TELEMETER APPARATUS FOR COUNTING A HEART RATE

[75] Inventor: Hirokazu Sasagawa, Tokyo, Japan

[73] Assignee: Nihon Kohden Corporation, Tokyo, Japan

[21] Appl. No.: 985,158

[22] Filed: Dec. 3, 1992

[30] Foreign Application Priority Data

Dec. 3, 1991 [JP] Japan ................. 3-319291

[51] Int. Cl.$^5$ ............................... A61B 5/04
[52] U.S. Cl. ................... 128/707; 128/903; 128/706
[58] Field of Search ............. 128/706, 707, 696, 903

[56] References Cited

U.S. PATENT DOCUMENTS

| | | | |
|---|---|---|---|
| 4,830,021 | 5/1989 | Thornton | 128/707 |
| 4,860,763 | 8/1989 | Schminke | 128/707 |
| 4,976,424 | 12/1990 | Sargeant et al. | 128/707 |
| 5,163,439 | 11/1992 | Dardik | 128/707 |

*Primary Examiner*—William E. Kamm
*Assistant Examiner*—Scott M. Getzow
*Attorney, Agent, or Firm*—Sughrue, Mion, Zinn, Macpeak & Seas

[57] ABSTRACT

A telemeter apparatus for counting a heart rate is provided which can accurately measure a heart beat signal without being affected by a radio interference between adjacent exercise test systems. A telemeter apparatus for counting a heart rate has: a transmitter unit to be attached to a subject using an exercise test system and for transmitting from a transmitting coil a heart beat signal detected from the subject, in the form of a magnetic signal; receiving coils respectively disposed at the both sides of a body of the exercise test system, and for receiving the magnetic signal transmitted from the transmitting coil; comparators for accepting the received signal from the corresponding receiving coil which has been amplified and rectified, and for comparing the accepted signal with a predetermined threshold level; an AND circuit to which output signals from the comparators are input; and a heart rate display unit for displaying a heart rate on the basis of an output signal from the AND circuit. The comparators, AND circuit, and heart rate display unit are disposed in the body of the exercise test system.

5 Claims, 4 Drawing Sheets

TELEMETER APPARATUS FOR COUNTING A HEART RATE

BACKGROUND OF THE INVENTION

This invention relates to a telemeter apparatus for counting a heart rate which transmits by wireless a heart rate detected from a subject using an exercise test system such as a treadmill, to the body of the exercise test system.

In an exercise test system such as a treadmill and an ergometer, a heart beat signal detected from a subject is transmitted by either of a wire system or a wireless system, to a data acquisition apparatus disposed in the exercise test system.

A wire system is used in an ergometer so that a pulse signal obtained from a subject is transmitted through a cable to a data acquisition apparatus.

Two possible systems are the ultrasonic system and the magnetic field system. In the ultrasonic system, electrodes for detecting an electrocardiograph (ECG) and attached to the body of a subject are connected through cables to a transmitter unit which is exposed to a receiver unit of a data acquisition apparatus, and a heart beat signal from the transmitter unit is transmitted in the form of an ultrasonic wave to the receiver. By contrast, in the magnetic field system, a transmitter unit attached to the body of a subject is not required to be exposed to the receiver, and a heart beat signal from the transmitter unit is transmitted through a magnetic field to a a receiver of data acquisition apparatus. The data acquisition apparatus is provided with a sole receiving coil for receiving the heart beat signal transmitted from a transmitting coil of the transmitter unit.

When the wire system is used for leg exercises practiced in an ergometer, etc., no problem will arise. In contrast, it is impossible to detect a pulse wave during the practice of total exercises in a treadmill. Therefore, the wire system is not adequate for the use in a treadmill. If the wire system is used in a treadmill, a pulse wave detected from a subject can be transmitted only during a low speed walking exercise and a pause of an exercise. When the wire system is used in an exercise test system, a cable for signal transmission causes a problem not only in that it is a hindrance to an exercise, but also in that, when this cable moves with the motion of a subject, it easily picks up noise from the background.

The ultrasonic system has problems in that an ultrasonic transmitter unit must be fixedly attached to the body of a subject while being exposed to the receiver, thereby making the attachment to the body cumbersome, and also is that the system is difficult to handle because its size is large. Moreover, the ultrasonic system has a disadvantage that, when something is interposed between the transmitter unit and the receiver unit, it is impossible to conduct data transmission.

In the conventional magnetic field system, since a data acquisition apparatus attached to an exercise test system is provided with only one receiving coil, there arise problems in that the apparatus is susceptible to being affected by noises and that radio interference between adjacent exercise test systems is liable to occur. Conventionally, therefore, it is necessary to separate adjacent exercise test systems from each other by an interval of at least 1.5 m, with the result that the number of exercise test systems which can be juxtaposed on one floor is restricted.

SUMMARY OF THE INVENTION

The present invention has been proposed to solve these problems in the prior art, and has an object of providing a telemeter apparatus for counting a heart rate which can accurately measure a heart beat signal without being affected by a radio interference between adjacent exercise test systems.

In order to accomplish the object, the telemeter apparatus for counting a heart rate according to the invention comprises: a transmitter unit to be attached to a subject using an exercise test system and for transmitting from a transmitting coil a heart beat signal detected from the subject, in the form of a magnetic signal; receiving coils respectively disposed at a plurality of portions of a body of said exercise test system and for receiving the magnetic signal transmitted from said transmitting coil; comparators for accepting the received signal from said corresponding receiving coil once it has been amplified and rectified, and for comparing the accepted signal with a predetermined threshold level; an AND circuit to which output signals from said comparators are input; and a heart rate display unit for displaying a heart rate on the basis of an output signal from said AND circuit, and said comparators, said AND circuit, and said heart rate display unit are disposed in the body of said exercise test system.

According to the arrangement described above, the comparators compare the accepted signal with the predetermined threshold level, whereby unwanted noise components which have a level lower than the threshold level can be eliminated.

When an interference wave transmitted from a neighboring exercise test system is received by only one of the receiving coils, the AND circuit does not produce an output signal. Therefore, effects caused by an interference wave can be eliminated by the AND circuit.

DETAILED DESCRIPTION OF THE PREFERRED EMBODIMENT

Figure 1:
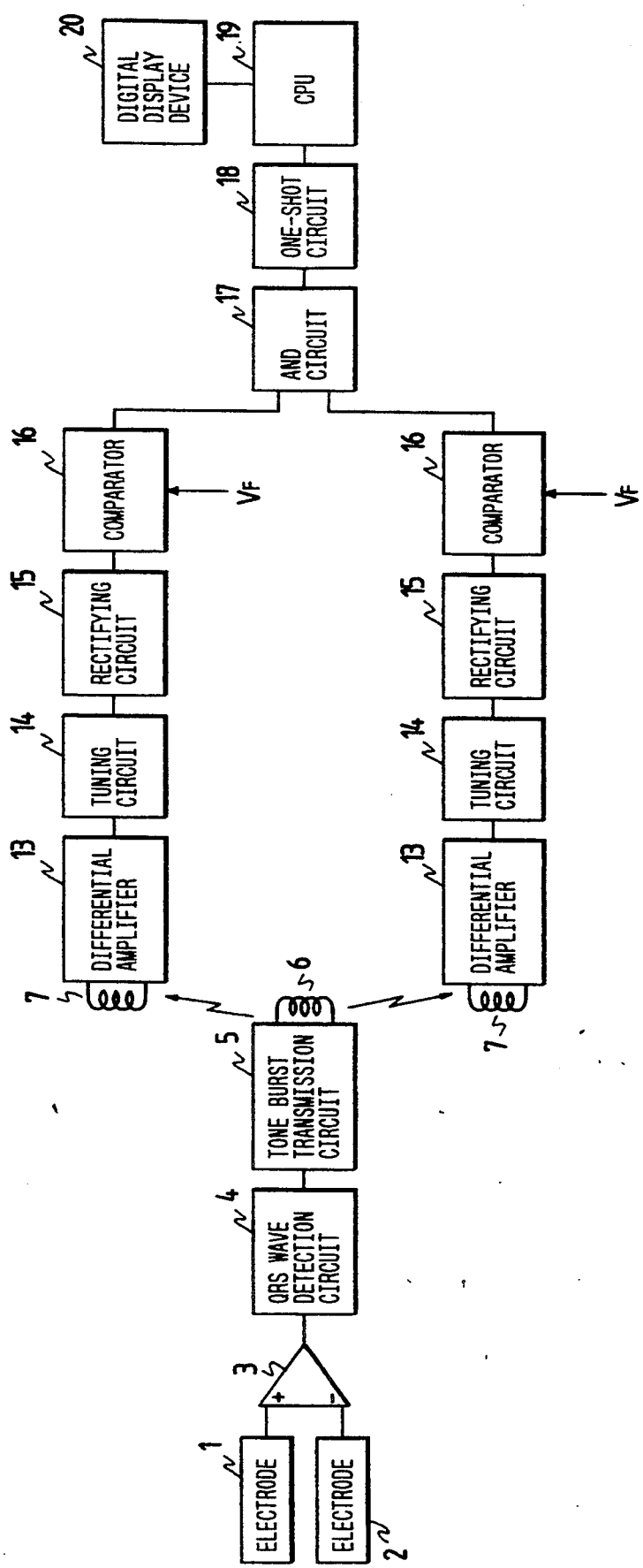
FIG. 1 is a block diagram of an embodiment of the telemeter apparatus for counting a heart rate according to the invention.

Hereinafter, specific embodiments of the telemeter apparatus for counting a heart rate of the invention will be described in detail with reference to the drawings. FIG. 1 is a block diagram of an embodiment of the telemeter apparatus.

Figure 2:
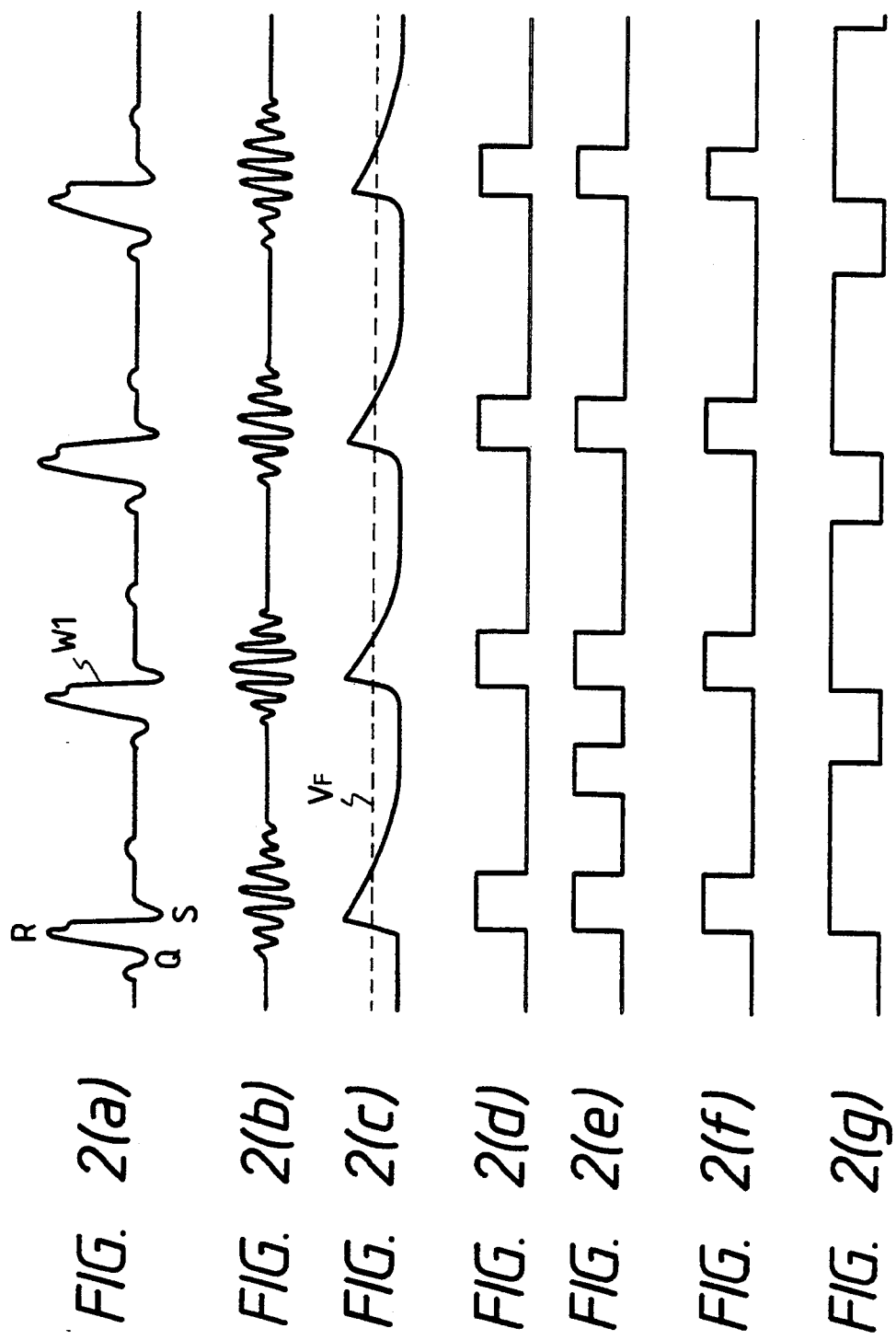
FIGS. 2 (a)–(g) show waveform charts illustrating the operation of the telemeter apparatus for counting a heart rate shown in FIG. 1.

In the embodiment, a ECG signal induced in electrodes 1 and 2 is amplified by an amplifier 3, and then sent to a QRS wave detection circuit 4. The QRS wave detection circuit 4 detects a QRS wave from an electrocardiograph W1 shown in (a) FIG. 2, and a signal indicative of the detection is sent to a tone burst transmission circuit 5. As shown in FIG. 2 (b), the tone burst transmission circuit 5 generates a tone burst transmission signal at a timing of the detection of a QRS wave. The tone burst transmission signal is transmitted as a magnetic signal of about 5 kHz from a transmitting coil 6. The amplifier 3, the QRS wave detection circuit 4, the tone burst transmission circuit 5 and the transmitting coil 6 are housed in a transmitter unit which is to be attached to, for example, the breast of a subject. The electrodes 1 and 2 are unitedly fitted to the transmitter unit.

Figure 3:
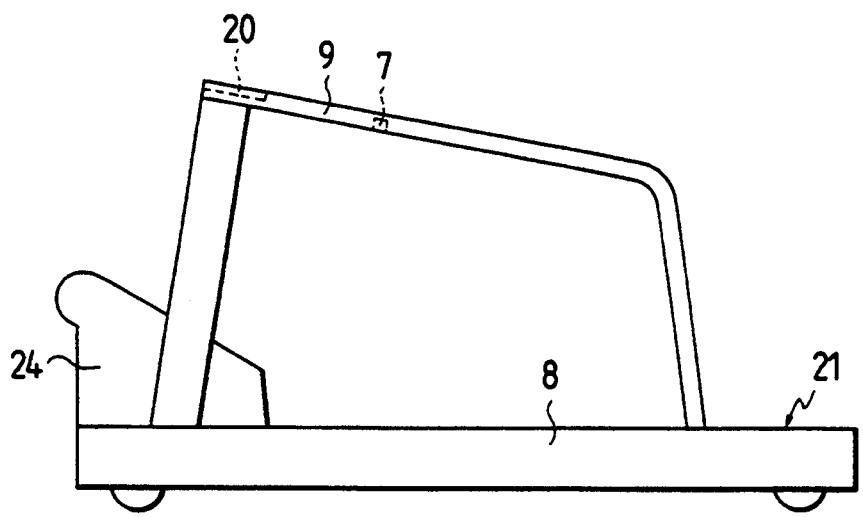
FIG. 3 is a side elevation view of a treadmill to which receiving coils are fitted.
Figure 4:
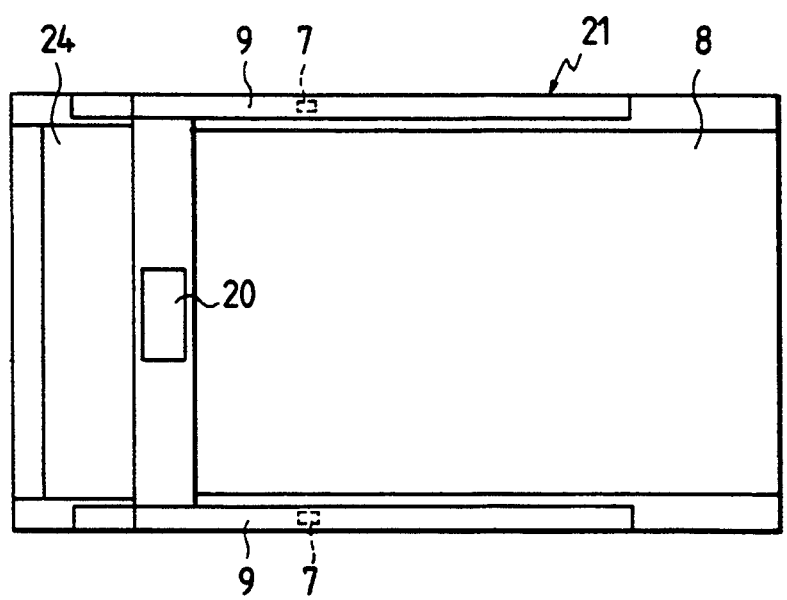
FIG. 4 is a plan view of the treadmill to which receiving coils are fitted.
Figure 5:
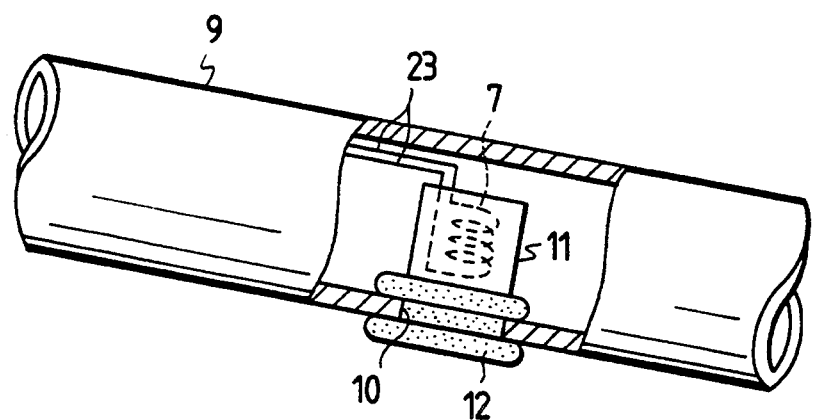
FIG. 5 is an enlarged view showing the portion of the treadmill at which a receiving coil is fitted.

Two receiving coils 7 are fitted on the both sides of the body of an exercise test system, respectively. FIGS. 3 to 5 show an example in which the receiving coils 7 are installed in a treadmill. In this example, fitting holes 10 for fitting a coil are formed at the lower and slightly front portion of side rails 9 which function as handrails of the both sides of a running area 8. The receiving coils 7 accommodated in a case 11 are respectively inserted through the fitting holes 10 into the side rails 9, and held by rubber bushes 12. The positions of fitting the receiving coils 7 on side rails 9 which are sloped upward toward the front end are determined in due consideration of the following two conditions: the receiving coils can approach the transmitter unit attached to the breast of a subject; and the receiving area can cover the rear portion of the running area 8. In this example, the fitting of the receiver coils near the front end of the side rails 9 improves the receiving sensitivity. The receiving area covered by the receiving coils 7 determines the threshold level of comparators 16 which are described later.

The tone burst signal in the form of a magnetic signal emitted from the transmitting coil 6 interlinks the two receiving coils 7 to be received by each of these coils 7. The received signals are amplified by differential amplifiers 13, and then sent to tuning circuits 14. The tuning circuits 14 comprise a generalized impedance converter (GIC) in which the sharpness Q can be set to be a large value, and selectively extract only the transmitting frequency of the transmitting coil 6. The received tone burst signals which have passed through the tuning circuits 14 are half-wave rectified by rectifying circuits 15, and thereafter sent to comparators 16. The comparators 16 compare the rectified signals shown in (c) of FIG. 2 with a threshold level $V_F$, whereby noise signals which are transmitted from the outside of the above-mentioned receiving area and are lower than the threshold level $V_F$ are eliminated.

Figure 6:
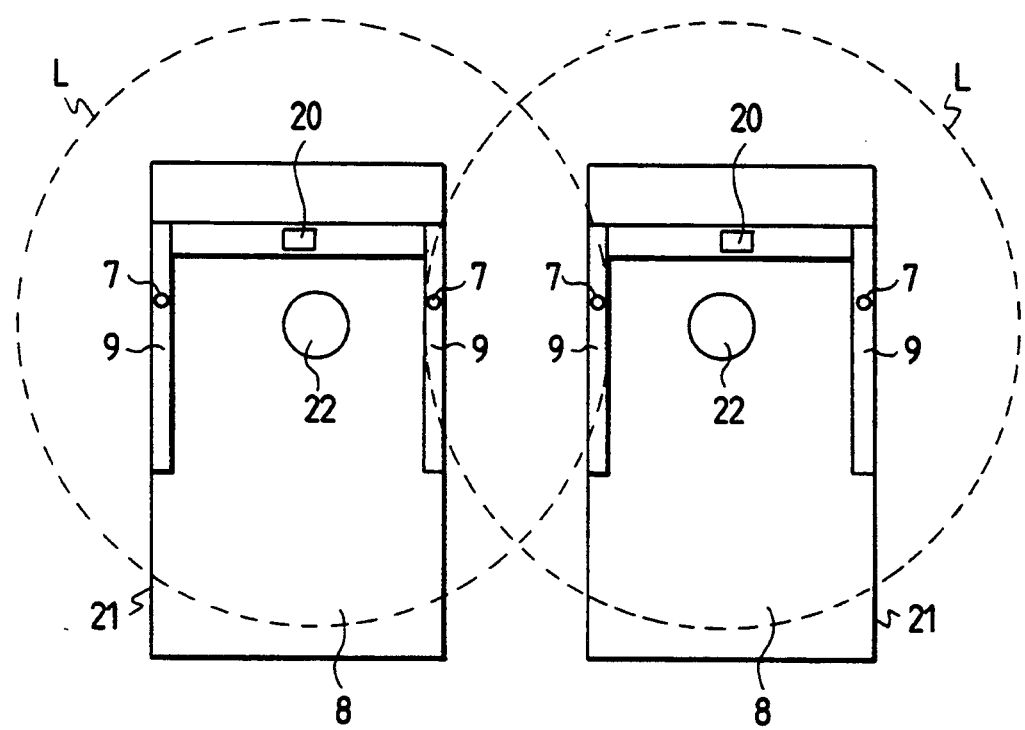
FIG. 6 is a diagram schematically illustrating signals transmitted from adjacent treadmills.

The rectangular signals ((d) of FIG. 2) output from the comparators 16 are input to an AND circuit 17. Only when the two input signals coincide with each other, the AND circuit 17 produces an output signal. In the case that an interference wave emitted from an adjacent treadmill 21 is received only one of the receiving coils 7 as shown in FIG. 6, the two signals input to the AND circuit 17 fail to coincide with each other as shown in (d) and (e) of FIG. 2, and therefore the output of the AND circuit 17 is inhibited so that the interference wave from an adjacent treadmill 21 is eliminated by the AND circuit 17. In the figure, 22 designates a subject, and L designates a transmitting area.

The output signal of the AND circuit 17 which is shown in (f) of FIG. 2 is sent to a one-shot multivibrator 18 (hereinafter, referred to as "one-shot circuit 18") to be converted to a rectangular signal shown in (g) of FIG. 2 and having a predetermined pulse width. The provision of the one-shot circuit 18 can eliminate noise components included in the heart beat signal.

The pulse signal from the one-shot circuit 18 is sent to a central processing unit (CPU) 19 which in turn processes the signal, whereby the heart rate of the subject is displayed on a digital display device 20. The receiver unit including the digital display device 20 is mounted in the front portion of the treadmill 21, and is connected to the receiving coils 7 through a signal cable 23 running inside the side rails 9. A mechanical housing 24 disposed in the front and lower portion of the treadmill accommodates a motor for driving the running area 8 and a jack for sloping the running area 8 at a predetermined angle.

The invention can be applied not only to a treadmill but also to other exercise test systems such as an ergometer.

As described above, according to the invention, a heart beat signal transmitted from a transmitting coil attached to a subject is received by two receiving coils disposed at two sides of an exercise test system, the received signals are rectified and then respectively compared with a threshold level by comparators, and these signals are thereafter input to an AND circuit so that, only when the two input signals coincide with each other, the AND circuit outputs the heart beat signal.

According to this configuration, when an interference wave emitted from an adjacent treadmill is received by one of the receiving coils, the two signals input to the AND circuit fail to coincide with each other, and therefore these signals are not treated as a normal signal. In this way, effects caused by an interference wave from an adjacent treadmill and by extraneous noise are removed.

Accordingly, the telemeter apparatus for counting a heart rate according to the invention has an advantage that it can correctly receive a heart beat signal without being affected by interference waves and other noise so that exercise test systems can be used in a close positional relationship, thereby allowing a plurality of exercise test systems to be juxtaposed.

Unlike an apparatus employing the ultrasonic transmission system, in the present apparatus, the employment of the magnetic transmission system eliminates the cumbersome requirement that the transmitter unit be attached so as to be exposed to the receiver, and enables the transmission to be conducted even when an obstacle exists between the transmitter and the receiver. Therefore, the present apparatus has an advantage that it can be more easily used.

What is claimed is:

1. A telemeter apparatus comprising:
   a transmitter device including means for transmitting a heart beat signal detected from a subject;
   at least two receiving coils each of which includes means for receiving said heart beat signal from said transmitter device;
   at least two comparators, each of said comparators including means for accepting a signal corresponding to said heart beat signal received by one of said receiving coils, means for comparing said signal with a predetermined threshold level, and means for outputting a resultant signal;
   an AND circuit including means for receiving said resultant signals and means for outputting an ANDed signal only when at least two of said resultant signals coincide in time; and a heart rate display unit including means for displaying a heart rate derived from said ANDed signal.

2. A telemeter apparatus as claimed in claim 1, said telemeter apparatus further comprising an exercise test system including means for allowing said subject to exercise while said heart rate is being displayed.

3. A telemeter apparatus as claimed in claim 1, wherein said heart beat signal is in the form of a magnetic signal with a predetermined frequency.

4. A telemeter apparatus as claimed in claim 2, wherein said receiving coils are disposed at a plurality of locations on said exercise test system.

5. A telemeter apparatus as claimed in claim 1, wherein said comparators, AND circuit, and heart rate display unit are comprised by said exercise test system.

* * * * *